United States Patent [19]

Soll et al.

[11] Patent Number: 5,400,249
[45] Date of Patent: Mar. 21, 1995

[54] APPARATUS FOR ASSESSING RELATEDNESS FROM AUTORADIOGRAMS

[75] Inventors: David R. Soll; Holly J. Hugart; Edward R. Voss, all of Iowa City, Iowa

[73] Assignee: University of Iowa Research Foundation, Iowa City, Iowa

[21] Appl. No.: 859,924

[22] Filed: Mar. 27, 1992

[51] Int. Cl.⁶ .................. G06F 15/42; G06F 15/66
[52] U.S. Cl. .................. 364/413.13; 364/413.01; 364/498; 382/34; 356/303; 324/312
[58] Field of Search .............. 364/413.01, 413.13, 364/497, 498; 382/34; 324/312; 356/303

[56] References Cited

U.S. PATENT DOCUMENTS 4,885,697 12/1989 Hubner .................. 364/497
4,970,672 11/1990 Snodgrass .................. 364/709.12

Primary Examiner—Gail O. Hayes
Assistant Examiner—J. L. Hazard
Attorney, Agent, or Firm—Kent A. Herink; Brian J. Laurenzo; Brett J. Trout

[57] ABSTRACT

Apparatus and method for assessing relatedness from autoradiograms. A scanner reads and digitizes the one or more banded lanes of an autoradiogram and communicates the information to a digital computer. The information is processed and analyzed to rationalize the banded lanes with a standard. Similarity coefficients and dendrograms of relatedness are generated.

4 Claims, 7 Drawing Sheets

Microfiche Appendix Included
(3 Microfiche, 281 Pages)

APPARATUS FOR ASSESSING RELATEDNESS FROM AUTORADIOGRAMS

BACKGROUND OF THE INVENTION

The invention relates generally to analyzing autoradiograms for relatedness of materials distributed in rows on the autoradiograms and, more specifically, to a computer-assisted apparatus for automatically analyzing autoradiograms and generating similarity coefficients between rows which are presented as a matrix, as a histogram, as a dendrogram, or as any combination thereof.

Gel electrophoresis is useful for sorting molecules by size. Mixtures containing proteins of different sizes, RNA's of different sizes, or DNA fragments of different sizes are loaded on gels and separated electrophoretically. In the case of DNA fragments, the major application of this invention, DNA fragments are separated primarily according to size with smaller fragments closer to the anode. The fragments are hybridized with a radiolabeled tag, usually a moderately repetitive sequence. By placing a sheet of X-ray film adjacent to the gel, or a blot of the gel, bands are resolved which correspond to fragments hybridized with the radiolabeled probe. This provides a pattern of bands, differing in size and intensity, which can be analyzed and compared visually by a researcher or optically by a scanner.

Although analysis of DNA fragments by gel electrophoresis is used for many purposes, analysis of banding patterns is most commonly used to "fingerprint" organisms such as viruses, bacteria, fungi, plants and, more recently, animals, including humans. DNA fingerprinting is useful for testing whether particular genetic sequences are present or are polymorphic, and so may be used as an epidemiological tool for following the etiological vector of a particular infection, identifying the source of infection, identifying a genetically based disease, or measuring the genetic similarity of two individuals, or strains, in a common species.

The characterization of strains of microorganisms is most widely accomplished by collecting and comparing phenotypic traits such as serotypes, resistance to chemicals, assimilation patterns, and colony or streak morphology. Phenotypic-based characterization systems, however, run the risk of grouping strains of microorganisms that are phenotypically similar but genetically unrelated. The converse, separating genetically related strains that are phenotypically dissimilar, can also result. DNA fingerprinting provides a far more meaningful route for typing strains since it compares genetic rather than phenotypic information. Unfortunately, the analysis of autoradiograms requires a great deal of time and effort. Moreover, autoradiograms often produce rows, or lanes of bands, which curve or are distorted, including lanes of differing length, lanes in which corresponding bands of the same fragments are resolved at shifted locations, variations in band intensity between runs, and so on. Considerable experience and skill is often required of the researcher, accordingly, to ensure that a valid analysis is being performed. Further, the human visual analysis process is inherently subjective such that differences in analysis may occur between researchers, and very limited when the number of strains being compared increases dramatically.

The specification of this invention includes a microfiche appendix under 37 C.F.R. §1.96 of 3 microfiche comprising a total of 281 frames. The appendix is a print-out in object code of the computer software program which is a part of this invention.

SUMMARY OF THE INVENTION

The invention consists of an apparatus for automatically analyzing autoradiograms produced by gel electrophoresis. The autoradiograms are digitized by a scanner that communicates the information to a computer. A graphics and analysis software package is used by the computer to discriminate between the lanes or rows of the autoradiogram, to separate the lanes, to straighten the lanes, to compensate for distortion, to process and eliminate defects from the image, and to scan each lane. The computer also uses the software to generate similarity coefficients between the lanes or any subset of lanes to generate matrices of the similarity coefficients, to generate histograms or dendrograms based on the similarity coefficients, and to generate such matrices, histograms, and dendrograms on any set of lanes in its library. The invention is useful, for example, in epidemiological studies of strain variability, in evolutionary studies, in analyzing protein fingerprinting patterns for forensic analysis, and in the study of very large restriction fragment length polymorphism patterns in the human genome project.

The invention can be applied to assess relatedness between individuals or strains of any organism for which effective fingerprinting methods have been developed. In doing etiology and epidemiology studies (such as in Candidiasis or in newly observed drug-resistant tuberculosis strains), the computer-assisted method for storing Southern blots (or other blots of protein fragments) and comparing data between large numbers of strains is a crucial component of the analysis.

An object of the present invention is to provide an apparatus for automatically assessing the relatedness of samples of protein fragments resolved by gel electrophoresis.

Another object of the invention is to provide an apparatus for automatically generating matrices of similarity coefficients for complex banding patterns generating from Western, Southern, or Northern blots.

A further object of the invention is to provide an apparatus for automatically generating histograms and dendrograms from the matrices of similarity coefficients.

Yet another object of the invention is to provide an apparatus for accurately reading lanes and bands of autoradiograms, processing the lane and band information to assure consistent analysis, and storing in a library the analyzed information for future comparison with such information from other autoradiograms.

These and other objects of the invention will be made apparent upon a review of the accompanying specification, drawings and claims.

DETAILED DESCRIPTION OF A PREFERRED EMBODIMENT

Figure 1:
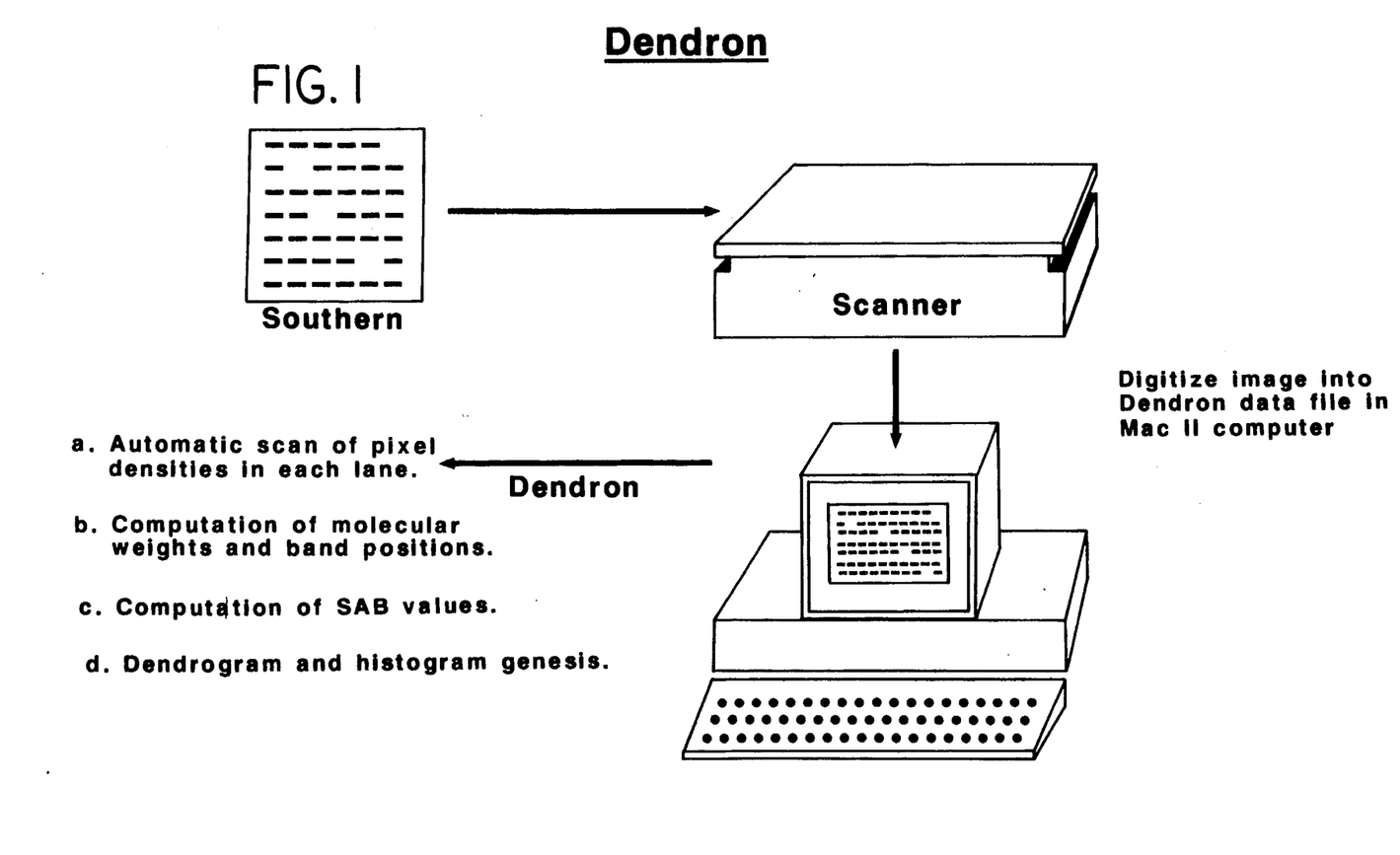
FIG. 1 is a schematic representation of the apparatus of the present invention.

The invention utilizes an optical scanner 20 to scan and digitize an autoradiogram 30 (FIG. 1). The autoradiogram 30 may be either the X-ray film itself or a photographic print. The scanner 20 will read an X-ray film autoradiogram by transmitted light and a photographic print by reflected light. The digitized image information from the scanner 20 is communicated to a computer 40 which uses a graphics and analysis software program to process, normalize and analyze the digitized image and to generate similarity values between the rows or lanes of the autoradiogram 30. The analyzed information of the autoradiogram 30 is stored in a library of the computer 40 to create a database of information from the banding patterns in the lanes. Information from a sample can be compared against any subset of samples in the library. Similarity coefficients between the selected samples are generated and displayed either as a matrix, as a histogram, or as a dendrogram 50 which is representative of the relatedness of the selected samples.

The invention will be described by way of an example involving eight samples of the fungus *Candida albicans*, a major fungal pathogen which is difficult to type accurately using phenotypic-based systems because of the ability of most *C. albicans* strains to switch reversibly and at high frequencies among a number of general phenotypes. Schmid, J. et al. *J. Clin. Microbiol.* 28:1236–43 (1990). A method of typing *C. albicans* strains at the genetic level has been developed. Endonuclease-digested cellular DNA is hybridized with radiolabeled probes of moderately repetitive sequences on Southern blots, generating complex patterns of 15 to 25 bands of diverse intensities which appear to be relatively specific for different strains. Scherer, S., and D. A. Stevens. *Proc. Natl. Acad. Sci. USA* 85:1452–56 (1988); Soll, D. R. et al. *J. Clin. Microbiol.* 7:681–90 (1989). Repetitive sequences which have been demonstrated to provide effective fingerprinting probes include Ca3 from *C. albicans*. Soll, Ibid. The patterns of the Ca3 probe appear to be stable enough during extended periods of cell multiplication to be useful in identifying the same strain isolated at different times during the course of an infection and variable enough to discriminate different strains at a single site of infection. The patterns are also stable after phenotypic switching has occurred.

The moderately repetitive sequences may be used, as in the example, to fingerprint strains in epidemiological studies by calculating similarity values between patterns of different strains based on band positions and intensities in Southern blot hybridization patterns by generating matrices of the similarity values, and by generating dendrograms for grouping strains according to pattern similarity. To assist in handling the large number of strains required for a valid study, the automatic, computer-assisted apparatus of the present invention was developed.

In the present example, eight strains of *C. albicans* were isolated and identified with the following labels: RP2IVW2, RP212VW, RP213VWSM, RP213VWL, RP213AN, RP214VW, RPZSI1GP, and RPZSTI1BTZ. In brief, DNA was prepared from each strain whereby 5 ml. of cell culture was washed and suspended in 1 ml. of a solution containing 1M sorbitol, 50 mM potassium phosphate (pH 7.5), 0.1% beta-mercaptoethanol, and 40 U of Zymolase (ICN Biomedicals, Inc., Lisle, Ill.). Spheroblasts were lysed in diethylpyrocarbonate solution, and the DNA was ethanol precipitated from the supernatant of a potassium acetate precipitation. DNA was suspended in 0.1 ml of TE buffer (10 mM Tris hydrochloride, 1 mM EDTA [pH 7.41]) containing 10 ug of RNase A. After two subsequent precipitations with 2-propyl alcohol, DNA was stored in TE buffer. DNA was measured by ethidium bromide dot quantitation and digested with 6 U of EcoRI enzyme (New England BioLabs, Inc., Beverly, Mass.) per ug for 4 h. A sample containing 2.7 ug of DNA was separated on a 0.8% agarose gel. DNA was then transferred to a nitrocellulose membrane by capillary blotting and immediately fixed by UV irradiation.

Figure 2:
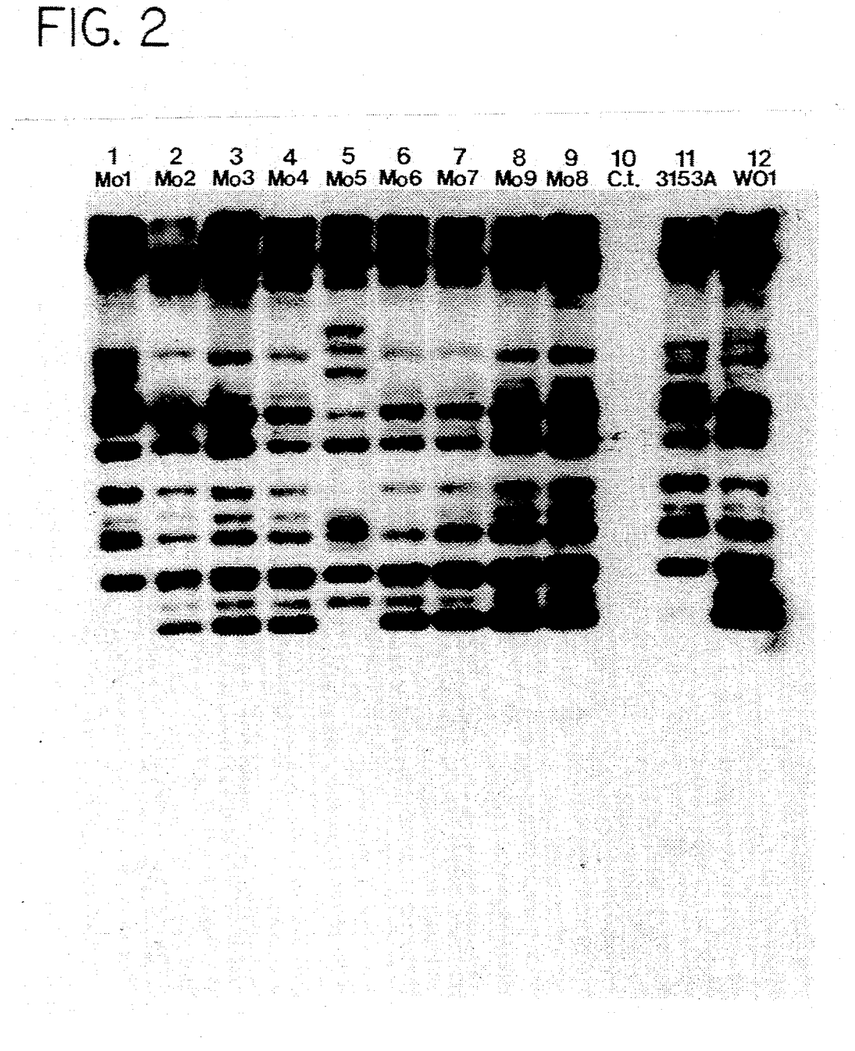
FIG. 2 is a photograph of an original Southern blot hybridization pattern for analysis by the invention.

Clone Ca3 was isolated from a gt10 library of partially EcoRI-digested DNA of strain 3153A by screening nitrocellulose filters with a hybridization probe of $^{32}P$-labeled, nick-translated, unfractionated DNA of strain 3153A. The repeat sequence consisted of 11 kilobases (kb) in a 15-kb *C. albicans* genomic fragment. This probe was nick translated with $[^{32}P]CTP$. Hybridization was performed with $3 \times 10^5$ cpm of Ca3 per ml at 65° C. in 0.9M NaCl-0.05M NAPO4-5 mM EDTA-5% dextran sulfate-0.3% sodium dodecyl sulfate (pH 7)-100 ug of denatured calf thymus DNA per ml. After incubation, hybridization membranes were washed and pressed against XAR-S film (Eastman Kodak Co., Rochester, N.Y.) with a Cronex Lightning-Plus (Du Pont Co., Wilmington, Del.) intensifying screen in a light-proof chamber. A sample X-ray film plate is illustrated in FIG. 2.

To determine the molecular sizes of Ca3 bands on a Southern blot hybridization pattern of strain 3153A DNA, a set of molecular size markers (1-kb ladder; Bethesda Research Laboratories, Inc., Gaithersburg, Md.) was run in a lane next to EcoRI-digested 3153A DNA in a Southern blot, and the molecular sizes of the major fragments that hybridized with Ca3 were determined. A sample of EcoRI-digested 3153A DNA was then included in a reference lane in every subsequent Southern blot of multiple *C. albicans* strains to determine the molecular sizes of bands in EcoRI-digested test DNAs. In the Southern blot depicted in FIGS. 4, 5, 7, and 10, the left-most and right-most lanes are both samples of the 3153A reference strain, and the eight intermediate lanes correspond to the eight independent isolates described above.

Figure 3:
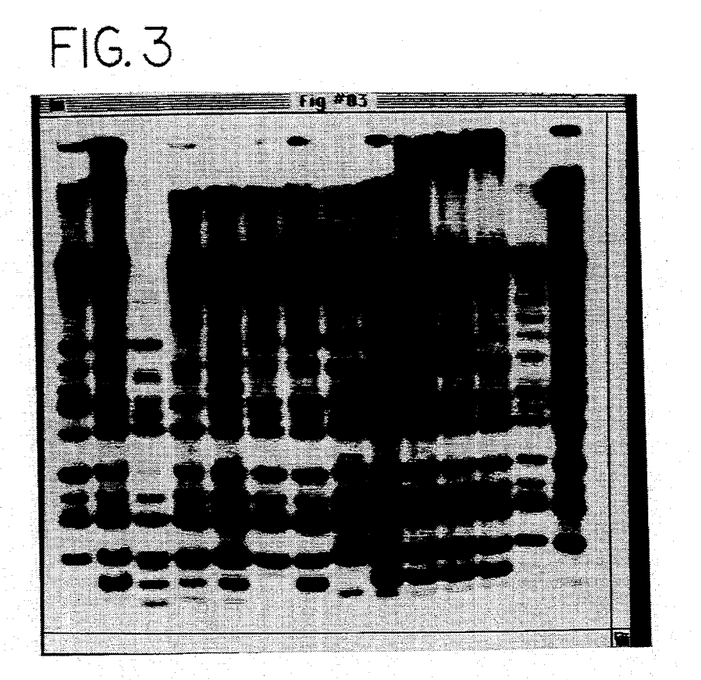
FIG. 3 is a digitized image of a Southern blot of eight strains of *Candida albicans* flanked by two reference strains that has been scanned into the computer.

The X-ray film of the Southern blot gel, or a print thereof on photographic paper, is read and digitized by a scanner (in the preferred embodiment a Sharp Electronics Model JX-450) 20 (FIG. 1). The digitized information is communicated into a PICT file of a Macintosh II fx personal computer (Apple Computer, Inc.) 40 (FIG. 1). The digitized image can be displayed on the computer screen in 256 gray levels (FIG. 3). As is evident in FIG. 3, the unprocessed Southern blot has lanes which are askew and curved, and common bands which should each be located on a horizontal line are displaced by diverse amounts. Further, entire lanes are vertically offset from others.

A graphics and analysis software program is run by the computer 40. A copy of its object code appears on the microfiche appendix which has been made a part of this application. The program includes a plurality of menus by which an operator can tailor the program to suit a diversity of specific applications. Once set to the desired operating parameters, the program will automatically process and analyze the digitized information from the scanned autoradiograms 30 (FIG. 1). However, at various points in the automatic process, the user can intervene to adjust operating parameters and to remove any artifacts.

Figure 4:
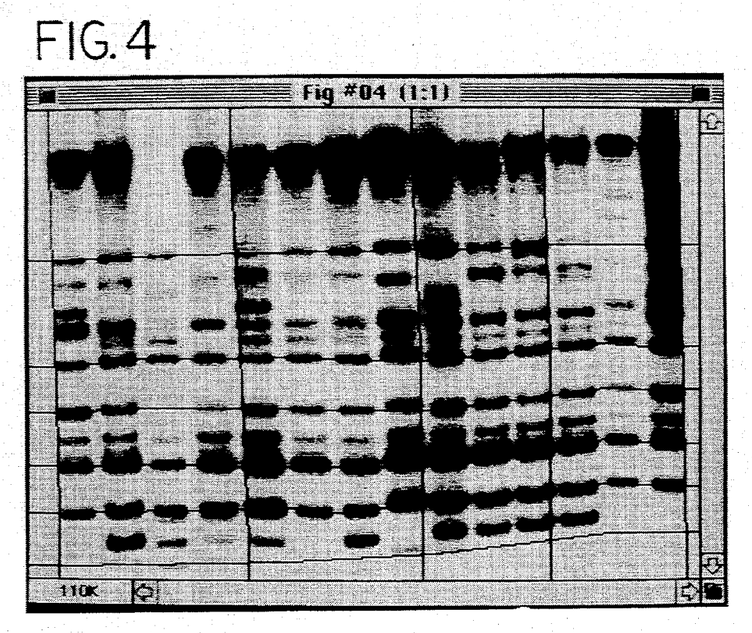
FIG. 4 illustrates horizontal and vertical lines drawn on the digitized blot of FIG. 3 to indicate distortion of the image.
Figure 5:
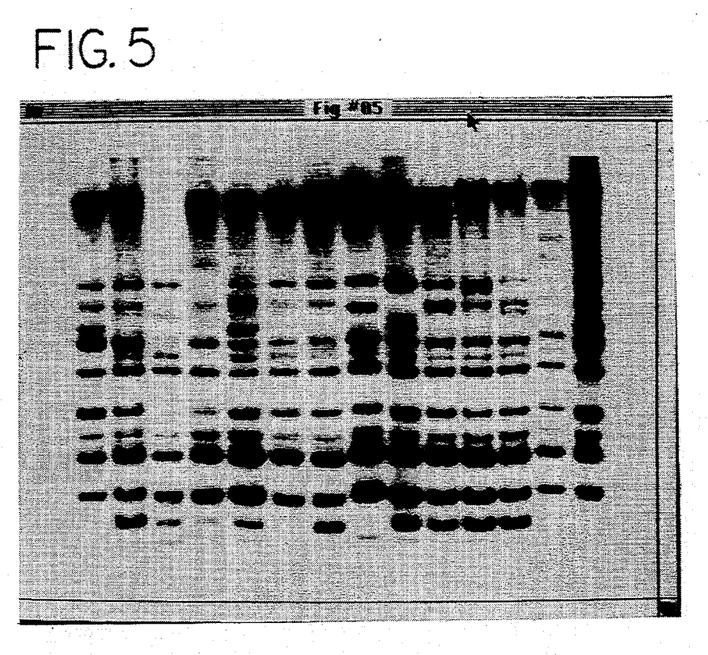
FIG. 5 illustrates the distortion-corrected blot of FIG. 4.

A series of vertical line segments are drawn on the image of the blot to separate the lanes and to identify sections of each lane (FIG. 4) which require rotational or nonlinear spatial adjustment to result in a series of straight lanes, one for each sample. A plurality of horizontal line segments are also drawn on the image of the blot to mark the top and bottom of each lane and common conserved bands (FIG. 4). The program will then align the vertical line segments to unwarp the lanes (FIG. 5). Common bands in the lanes still may be displaced from a desired common horizontal reference line by a small amount; these are aligned by subsequent processing described below.

Figure 6:
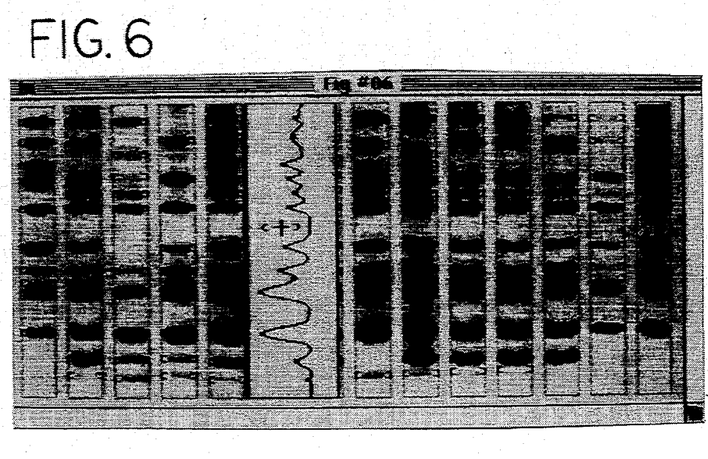
FIG. 6 illustrates the lanes of FIG. 5 identified by enclosing rectangles with the boundaries of the bands marked and a window displaying a densitometry graph of a selected lane.

Each of the lanes is then labeled and the bands detected (FIG. 6). The program will automatically detect the bands or it can be performed manually from densitometry graphs. The boundaries of the bands are labeled on the image of the blot (FIG. 6). The program creates densitometry graphs of each of the lanes and a user can elect to display the graph of a selected sample (the graph illustrated in FIG. 6 corresponds to the sample RP2I3VWL of the fifth lane). The densitometry graphs are useful in identifying common bands and in the scaling functions described below. The program allows user interaction to specify the width of any band, to remove or add bands, and to specify molecular weights based on a global standard. In the example, bands of less than 2.25 kb are excluded because they were faint under exposure conditions optimal for the more intense, large-molecular-size bands. A band of approximately 19 kb was also excluded since its position was identical to that of undigested DNA. The molecular sizes of the analyzed bands ranged from 2.25 to 17.0 kb.

Figure 7:
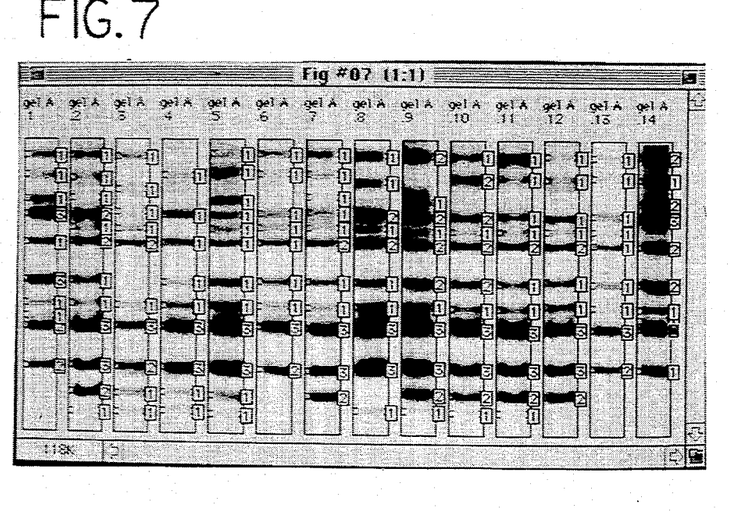
FIG. 7 illustrates the lanes of FIG. 6 wherein the bands have been labeled with assigned intensity class values.

The intensity of each band is scored automatically or manually by comparison to the intensities in the reference 3153A pattern. The relative loading intensity of the lanes is taken into account when automatically computing the band intensity. The program allows a user to specify the range of class values that will be used by the program in automatically assigning such class values to each band in the blot. In the example, hybridization was scored in arbitrary units: 0 U, absence of a band; 1 U, weak hybridization; 2 U, medium hybridization; 3 U, strong hybridization (FIG. 7). In assigning class values, if a band was positioned in one lane at a particular molecular size and a particular intensity but no correlate band was observed in a second lane, the second lane was assigned a class value of 0 U for that band position.

Figure 8:
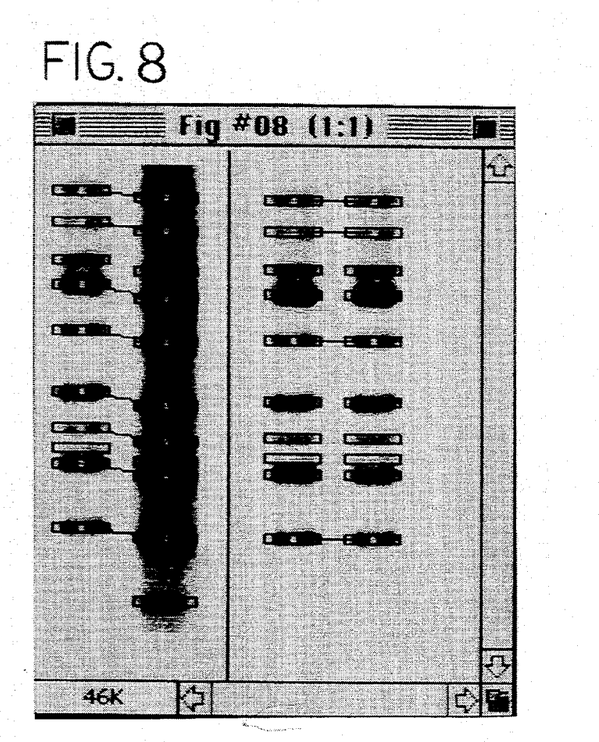
FIG. 8 illustrates two ways in which a local standard is normalized to a global standard.

To provide a method for correctly and consistently identifying bands in the sample strains, a global hybridization standard, Laboratory strain 3153A, is scanned into the computer. All subsequent blots are referred to this standard. On each blot, the local standard is matched to the global standard by a user employing a "stretch and slide" feature of the program. In FIG. 8a, the global standard is displayed to the left of the local standard. Although the two standards have many common bands, the lane of the local standard is considerably shorter than the lane of the global standard. The user specifies the top and bottom of the lane segment to be stretched to the desired length. The program then proportionally lengthens (or shortens) the lane segment. The lanes may also be moved (or slid) vertically. By using a combination of stretching and sliding, the local standard is matched to the global standard, as shown in FIG. 8b. An alternative matching method is provided wherein the user connects common bands (FIG. 8c) or internal standards directly.

Figure 9:
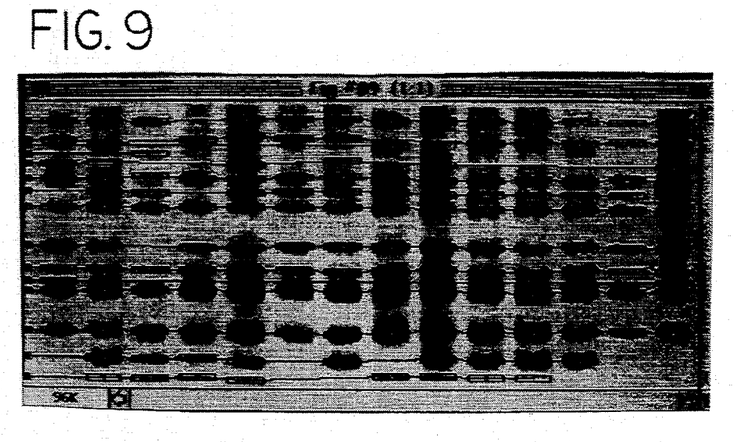
FIG. 9 illustrates the aligning of four lanes to a local standard and indicating new bands not found in the local standard.
Figure 10:
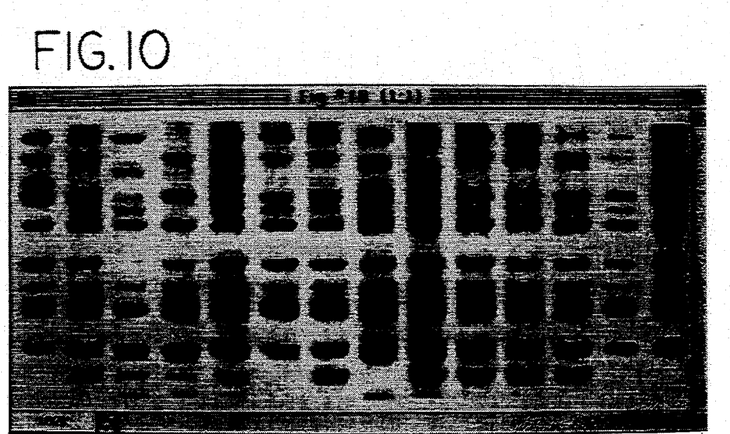
FIG. 10 illustrates the lanes of FIGS. 3–7 normalized to conform to the global standard.
Figure 11:
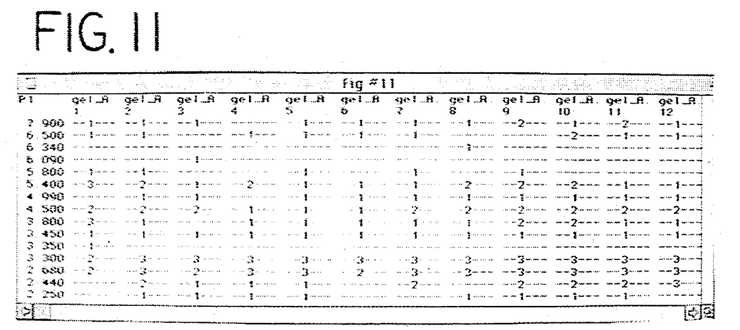
FIG. 11 is a text file representation of the lanes and bands of FIGS. 3–7 and 10 showing the lanes, bands, classes, and molecular weights of the autoradiogram.

Once the local standard has been matched to the global standard, using any combination of the two techniques described above, the "stretch and slide" and direct lining-up methods are used to match each lane to the local standard using conserved bands and molecular weights are assigned. The information on each lane is now entered into a library file or database of the computer to permit it to be included in future comparisons with other strains. If new bands not previously observed are found, they are indicated on the display and logged in the global standard. In FIG. 9, lanes of four other strains that have new bands are displayed for illustrative purposes. The program then normalizes the image of the blot to conform to the global standard (FIG. 10), and will allow a user to overlay lanes for a direct visual comparison. The user may also direct the program to create a text file showing the bands, assigned class values of intensity, and molecular weight on the blot that has been entered into the database (FIG. 11). Text files on strains previously entered into the database can be easily accessed.

To assess the similarity between patterns of two strains, A and B, a similarity coefficient ($S_{AB}$) is calculated using the following formula:

$$S_{AB} = \sum_{i=1}^{k}(a_i + b_i - |a_i - b_i|) / \sum_{i=1}^{k}(a_i + b_i)$$

where $a_i$ and $b_i$ are the intensities of band i in patterns A and B, respectively, and k is the number of bands. If the patterns for strains A and B are identical (i.e., all major bands are in the same position and every band intensity is comparable), the $S_{AB}$ value is 1.0. If the patterns for strains A and B are completely nonidentical (i.e., all major bands are in different positions), then the $S_{AB}$ value is 0.0.

Figure 12:
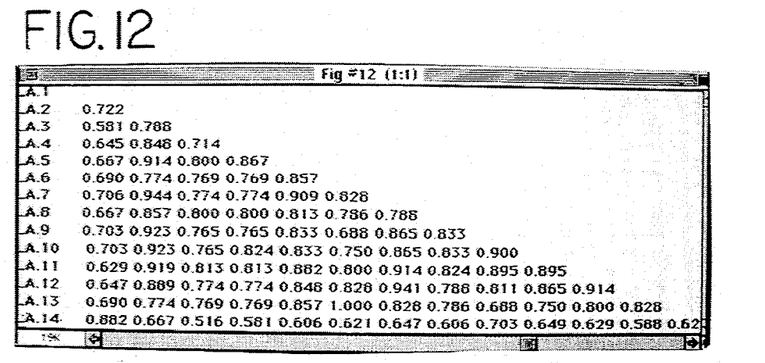
FIG. 12 is a matrix of similarity values of the lanes of the autoradiogram of FIGS. 3–7, 10 and 11.

A lower triangular matrix of $S_{AB}$ values for the blot of FIGS. 3–7 and 10 is illustrated in FIG. 12. The main diagonal (which would be entries of all 1.0) and the symmetrical upper half are redundant and not shown.

Figure 13:
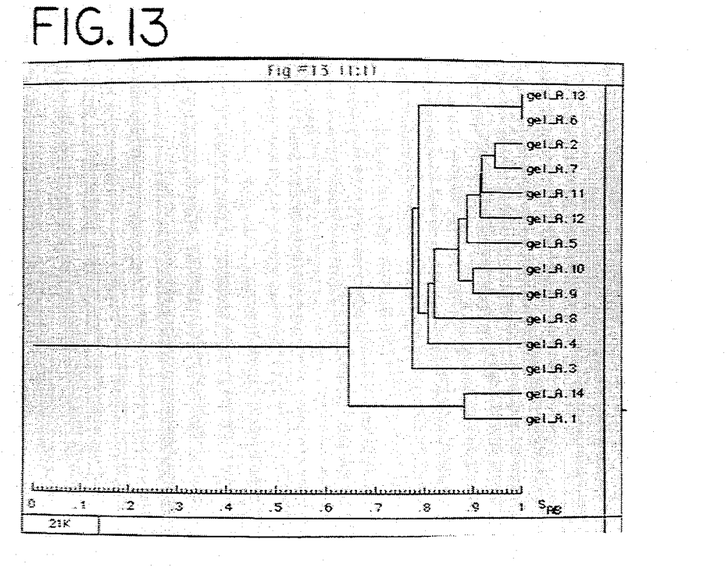
FIG. 13 is a dendrogram of the strains used to create the autoradiogram of FIGS. 3–7 and 10–12 and showing the relationship of the strains based on similarity.

For an analysis of relationships among a number of strains, the program generates dendrograms by the unweighted pair group method. In dendrogram construction, the pair of strains with the highest $S_{AB}$ value is grouped into a unit with a connecting point corresponding to its $S_{AB}$ value. The process continues in the direction of lower $S_{AB}$ values, with units being considered strains. The $S_{AB}$ value for a strain and a unit or for two units is taken to be the average of the $S_{AB}$ values of the members of the two entities. A dendrogram of the eight strains in the example is illustrated in FIG. 13. Dendrograms can be generated for all strains, or any subset of strains, in the database.

While the particular example of assessing similarity between eight strains of *C. albicans* has been described in detail, the invention is applicable to a limitless number of strains of any organism, and to the analysis of any set of autoradiograms.

Although the invention has been described with respect to a preferred embodiment thereof, it is to be also understood that it is not to be so limited since changes and modifications can be made therein which are within the full intended scope of this invention as defined by the appended claims.

I claim:

1. A computer implemented method of assessing relatedness from autoradiograms including one or more banded lanes having a vertical, lengthwise dimension and a horizontal, widthwise dimension, each banded lane being distorted in both of the dimensions, the method comprising the steps of:

(a) digitizing an autoradiogram, including the banded lanes;
   (b) averaging in the computer said digitized lanes over a substantial portion of the widthwise dimension to identify the bands of said digitized lanes;
   (c) comparing in the computer said identified bands to reference bands of a standard banded lane and generating in the computer a set of conserved bands that includes those identified bands that generally correspond to said reference bands;
   (d) dividing in the computer said digitized lanes into sections separated at vertical positions between said conserved bands, each of said sections having a length and a position;
   (e) aligning in the computer one or more of said sections to straighten each banded lane along a vertical axis;
   (f) adjusting in the computer the length and position of one or more of said sections to bring said conserved bands into horizontal alignment with said reference bands;
   (g) generating in the computer similarity coefficients between said lanes; and
   (h) generating dendograms based on said similarity coefficients.

2. The method of claim 1, wherein the bands of the lanes are variations in intensity of the autoradiogram, further comprising the step of normalizing in the computer the intensity of the banded lanes with a reference intensity of a standard.

3. The method of claim 1, further comprising the step of generating in the computer an autoradiogram from said straightened and aligned lanes.

4. A computer implemented method of assessing relatedness from autoradiograms including one or more lanes having a background of generally low intensity and a plurality of bands of higher intensity than the background, wherein the banded lanes have a vertical, lengthwise dimension and a horizontal widthwise dimension, the method comprising the steps of:

(a) digitizing an autoradiogram, including the banded lanes;
   (b) averaging in the computer said digitized lanes over a substantial portion of the widthwise dimension to create a tracing of the averaged intensity of said lane along the lengthwise dimension and to identify the bands of each lane;
   (c) comparing in the computer said identified bands to reference bands of a standard banded lane and generating in the computer a set of conserved bands that includes those identified bands that generally correspond to said reference bands;
   (d) classifying in the computer said conserved bands by relative intensity into a plurality of band classes;
   (e) adjusting in the computer the intensity of bands on each of said band classes in proportion with the intensity of the background of each lane relative to the background of a reference standard and in proportion with the intensity of said conserved bands of each lane relative to the intensity of corresponding bands of said reference standard;
   (f) generating in the computer similarity coefficients between said lanes based on the position and class range of each of said conserved bands; and
   (h) generating dendograms based on said similarity coefficients.

* * * * *

UNITED STATES PATENT AND TRADEMARK OFFICE
CERTIFICATE OF CORRECTION

PATENT NO : 5,400,249
DATED : March 21, 1995
INVENTOR(S) : David R. Soll; Holly J. Hugart; Edward R. Voss

It is certified that error appears in the above-identified patent and that said Letters Patent is hereby corrected as shown below:

Column 6, Line 55: formula should read as follows:

$$S_{AB} = \sum_{i=1}^{k} (a_i + b_i - |a_i - b_i|) / \sum_{i=1}^{k} (a_i + b_i)$$

Signed and Sealed this

Twenty-seventh Day of March, 2001

*Attest:*

NICHOLAS P. GODICI

*Attesting Officer*  *Acting Director of the United States Patent and Trademark Office*